(12) United States Patent
Nimal

(10) Patent No.: US 8,862,258 B2
(45) Date of Patent: Oct. 14, 2014

(54) BIOMEDICAL DEVICE, METHOD FOR MANUFACTURING THE SAME AND USE THEREOF

(76) Inventor: Didier Nimal, Gif-sur-Yvette (FR)

(*) Notice: Subject to any disclaimer, the term of this patent is extended or adjusted under 35 U.S.C. 154(b) by 93 days.

(21) Appl. No.: 13/355,845

(22) Filed: Jan. 23, 2012

(65) Prior Publication Data

US 2012/0165954 A1 Jun. 28, 2012

Related U.S. Application Data

(63) Continuation-in-part of application No. PCT/EP2010/058941, filed on Jun. 23, 2010.

(51) Int. Cl.
*G06F 19/00* (2011.01)
*A61L 27/12* (2006.01)
*A61L 27/56* (2006.01)

(52) U.S. Cl.
CPC *A61L 27/12* (2013.01); *A61L 27/56* (2013.01)
USPC .......................................................... 700/98

(58) Field of Classification Search
USPC .......................................................... 700/98
See application file for complete search history.

(56) References Cited

U.S. PATENT DOCUMENTS

| | | | |
|---|---|---|---|
| 4,863,538 A | 9/1989 | Deckard | |
| 6,454,811 B1* | 9/2002 | Sherwood et al. | 623/23.76 |
| 6,993,406 B1 | 1/2006 | Cesarano, III | |
| 8,048,150 B2* | 11/2011 | Weber et al. | 623/1.42 |
| 2003/0074096 A1 | 4/2003 | Das et al. | |
| 2003/0114936 A1 | 6/2003 | Sherwood et al. | |
| 2003/0175410 A1* | 9/2003 | Campbell et al. | 427/2.24 |
| 2005/0177238 A1 | 8/2005 | Khandkar | |
| 2006/0052875 A1 | 3/2006 | Bernero et al. | |
| 2006/0198939 A1* | 9/2006 | Smith et al. | 427/2.1 |
| 2007/0003753 A1* | 1/2007 | Asgari | 428/315.5 |
| 2007/0118243 A1* | 5/2007 | Schroeder et al. | 700/118 |
| 2007/0183918 A1* | 8/2007 | Monsheimer et al. | 419/1 |
| 2007/0210493 A1 | 9/2007 | Takahashi et al. | |

FOREIGN PATENT DOCUMENTS

WO 2009/053835 4/2009

OTHER PUBLICATIONS

International Search Report dated Feb. 4, 2011, corresponding to International Application No. PCT/EP2010/058941.

* cited by examiner

*Primary Examiner* — Michael D Masinick
(74) *Attorney, Agent, or Firm* — Young & Thompson

(57) ABSTRACT

A three-dimensional biomedical device having an osteoinductive first area with a controlled porosity and a second area, which is produced by laser technology from a powder including one of ceramics, metals, metal alloys, bioactive glasses, lead zirconate titanate and biocompatible polymers, or mixtures thereof. The ratio of the porosities from the second area to the first area is equal or less than one, preferably from 0.001 to 0.9. A method for manufacturing the device for fitting in a bone defect, wherein a virtual object is designed with a computer-aid designed software, and the device is manufactured by laser technology including layering a powder onto a plate (7) so that a layer of a predetermined thickness is formed; the laser beam (8) selectively processes the powder to produce a processed layer, and, thus, layer after layer, the layers are joined together until the biomedical device is formed.

8 Claims, 1 Drawing Sheet

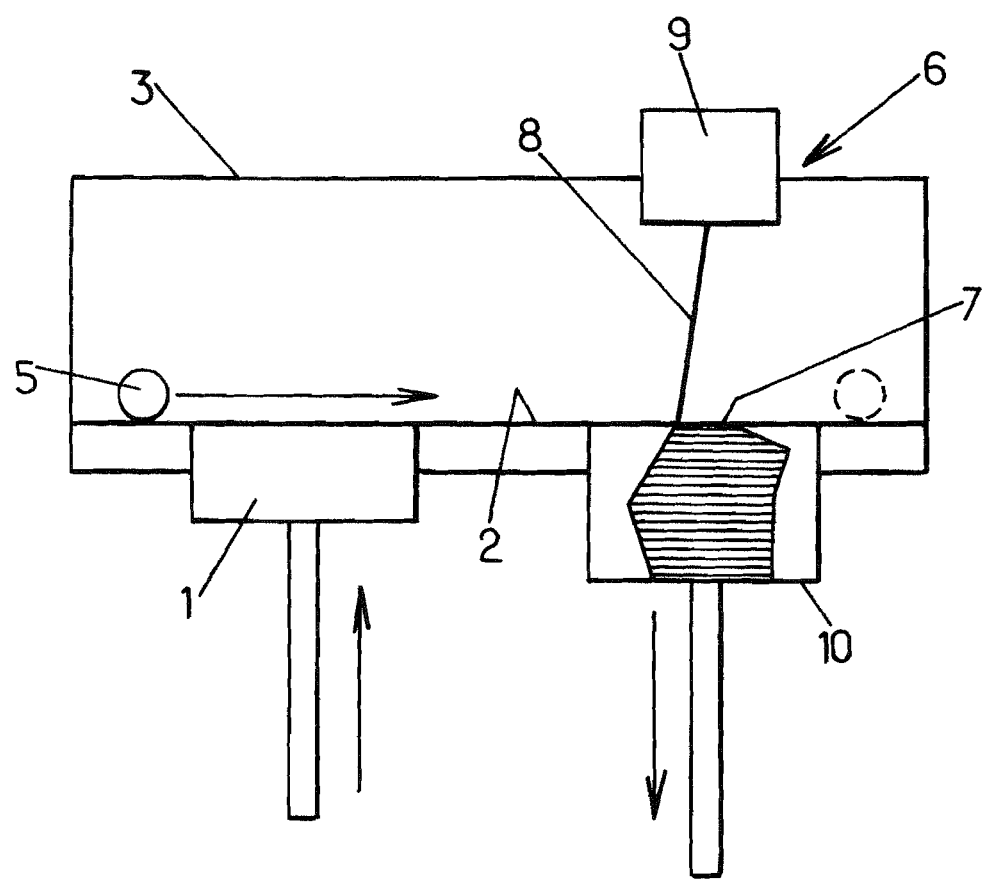

BIOMEDICAL DEVICE, METHOD FOR MANUFACTURING THE SAME AND USE THEREOF

FIELD OF INVENTION

This invention relates to the field of the manufacture of implants for medical and/or orthopedic applications, such as for example prostheses, orthodontia, bone implants, preferably cranial implants. More precisely, the present invention relates to a method of manufacturing a biomedical device from ceramic or metal powder, using a laser technology.

BACKGROUND OF THE INVENTION

The growing search for new materials for orthopedic or reconstruction surgery, lead to the development, in the last two decades, of biomedical devices based on ceramics, such as hydroxyapatite and tricalcium phosphate. These ceramic materials were recognized as biocompatible and as having an osseoconductive behavior, and were thus used for the repair or replacement of bone defects.

Aiming a controlled porosity of these materials while keeping satisfactory mechanical properties, remains the technical challenge of these biomaterials. Efforts in manufacturing porous ceramics with interconnected pores have been made in order to enhance tissue growth. It is known that a porous and interconnected structure allows new tissue to penetrate the substrate, and stimulates the growth of new bone tissue.

For example, WO2009/053835, as well as a number of the prior art documents in the field, reports a method to make biomedical devices with controlled porosity, involving the replication in ceramics of 3D-substrates such as polymeric substrates, which are eliminated at the end of the process by sintering. This method has the disadvantage of necessitating several steps, first for the manufacture of the substrate and second for the elimination/release of the substrate. Furthermore, the release of the substrate is susceptible to result in cracking phenomena on the thin walls of the piece. To avoid these drawbacks, additives are used. Most of the time, these additives are not biocompatible. Moreover, there is a remaining high risk that the step of elimination of the substrate may cause a distortion in the work piece due to variations of the dimensions during the warm-up. For these reasons, elimination of the substrate may be a hazardous step that the present invention intends to avoid.

The present invention is thus advantageous, in that the process of the invention involves direct laser treatment of the powder without use of a substrate, which is time effective, avoids the risk of distortion of the work piece, and is free of additives. Consequently, the product resulting from the manufacturing process of the invention is also free of additives.

Some prior art documents related to ceramic devices avoid the use of polymeric substrates and directly mix powders, such as for example, U.S. patent application 20070210493. This U.S. patent application reports the manufacture of porous ceramics based on slurry prepared from by mixing alumina particles, glass frit, silica particles, silica sol and water. This mixture is set in a plate, dried and sintered in order to obtain a hard and resistant ceramic. However, this method leads to a filter for filtering fluid such as liquid and gas or the like, and is not adapted for a biomedical device.

Further prior art relates to methods of manufacturing three-dimensional objects by laser technology. U.S. Pat. No. 4,863,538 for example, reports how to make a three-dimensional objet from a powder of plastic, metal, polymer, ceramic powders, or composite materials. The reported method is a layer-wise method: the powder is dispensed into a target area where the laser selectively sinters the powder to produce a sintered layer; the layers are joined together until the completed part is formed.

Technical Issue

There is thus still a need for simple methods for manufacturing biocompatible implants, avoiding multi-step processing. There is also a high expectation in this industry for safer and cost effective methods for manufacturing biocompatible implants avoiding the use of molds, which may lead to the need of further machining steps and/or to the use of substrate or binding agent. There is also a need for methods not involving the use of additives.

The present invention avoids the drawbacks of the prior art methods, as it is a one-step method for a direct manufacturing of a tridimensional object from a three-dimensional virtual object through laser technology, without using any mould.

The method of the invention is very advantageous in that it makes it easy to shape an implant perfectly matching the shape of the defect site and it does not involve the manufacturing of a specific mold for each defect. A close fit between the implant and defect site is desirable because (1) it can improve the healing of the defect after implantation, by for example facilitating the influx of cells, and (2) it ensure that the implant remains in the desired position within the defect. This invention is not limited in any way regarding the shape of the work piece, and makes it easy to manufacture complex, unique, customized work pieces, with an industrial scale. The method of the invention is also advantageous as it may utilize any kind of material suitable with laser technology, for the manufacture of the implant.

Another advantage of the method of the invention is to result, if desired, in a biocompatible material having a controlled porosity.

DEFINITIONS

The term "biomaterial" as used herein means a material that is biocompatible with a human or animal body. The biomaterial may be comprised within, or may be, an implant or tissue scaffold.

The term "porous" as used herein refers to a substrate that comprises pores holes or voids, rendering the biomaterial osteoconductive. Osteoconductivity typically refers to features associated with pores having a diameter equal or greater than approximately 10 micrometers, preferably from 10 to 1000 micrometers, more preferably from 100 to 800 micrometers, still more preferably from 200 to 600 micrometers, even more preferably 300 to 500 micrometers.

The term "porosity" refers to a measure of the void spaces in the biomaterial of the invention, and is measured as a fraction, between 0-1, or as a percentage between 0-100%. According to the present invention, porosity is measured with SEM, i.e. Scanning Electro Microscopy (microscope JSM 6300 of the JEOL company, tension 15 KV): samples of "first area" are invested in a polymethylmethacrylate resin, and then polished and made conductor by the depot a thin layer of Gold-Palladium; 8 images (×20 scale) are acquired for each sample. Porosity is then assessed by a image analysis software using a technique of grey thresholding. The same method is applied to assess the porosity of the <<second area>>.

The term "powder" refers to a material composed of very fine particles that are not cemented together.

The term "particle" as used herein means a fragment or small piece of material.

The term "non-resorbable" as used herein means substantially not susceptible to be absorbed or eliminated by an animal body, including human body, through a physiological process.

The term "implantable" as used herein means capable to be surgically grafted, inserted or embedded in an animal, including human, body.

The term "first area" as used herein means an area of the implant that is proximal and/or in contact with the borders or limits of the defect, and susceptible to be colonized in situ by the patient cells, such as for example the patient osteoblasts. According to an embodiment, all or part of the first area is colonizable by osteoblasts, and when colonized, has mechanical properties very close to the mechanical properties of the adjacent bone. Advantageously, the first area is colonized at its edge, which is very close or in conctact with the natural tissue when implanted. According to the invention, the osteoconductive porous first area is colonizable in situ with osteoblasts and behaves as a support for growth of osteoblasts.

The term "second area" as used herein means an area which may not be colonized in situ by the patient cells, because it is too distant from the borders or limits of the defect or because it is made of non-colonizable material, or because its low porosity does not make it possible for the cells to colonize. In an embodiment, the second area is tight.

The term "synthetic" as used herein means artificially produced

The term "substantially not degradable" means less than 10% of resorbability by year.

DETAILED DESCRIPTION

This invention thus relates to a three-dimensional biomedical device, having an osteoconductive first area with a controlled porosity and a second area, the device being produced by a laser technology from a powder comprising ceramics; and/or metals; and/or metal alloys; and/or bioactive glasses; and/or lead zirconate titanate; and/or biocompatible polymers and/or mixtures thereof.

Ceramics may be preferably selected from alumina or alumina derivative such as for example aluminosilicate; ceramic phosphates preferably tricalcium phosphate; apatite derivatives, preferably hydroxyapatite (including synthetic hydroxyapatite, more preferably substantially not degradable synthetic hydroxyapatite, carbonate-substituted hydroxyapatite, silicate-substituted hydroxyapatite); fluoroapatite or fluorohydroxyapatite or silicated apatite; zirconia, zirconia derivatives, zirconia-toughened alumina (ZTA), alumina-toughened-zirconia (ATZ), alumina-zirconia, ytria-zirconia (TZP), wallostonite.

Metal and/or metal alloy are preferably selected from titanium; titanium alloys such as for example titanium-aluminum-vanadium; chrome-cobalt and alloys thereof, titanenickel alloys such as for example nitinol, stainless steel Bioactive glasses are recognized as materials suitable for bone repair or replacement. Bioglasses preferred in the present invention are silicate type materials composed of $SiO_2$, CaO and optionally $Na_2O$, and/or $P_2O_5$. Preferred bioglasses are those as commercialized under the name "Bioglass45S5", or those having a composition as follows: 45-55% $SiO_2$, 10-25% ($K_2O+Na_2O$), 0-5% MgO; 10-25% CaO; 0-2% $P_2O_5$ and 0-1% $B_2O_3$ in weight, to the total weight of the bioglass. A preferred bioglass has the following composition: 45% $SiO_2$, 24.5% CaO and 24.5% $Na_2O$ and 6% $P_2O_5$ in weight to the total weight of the bioglass. Another preferred bioglass has the following composition: 53% $SiO_2$, 11% $K_2O$ and 6% $Na_2O$ 5% MgO 22% CaO and 2% $P_2O_5$ and 1% $B_2O_3$ in weight, to the total weight of the bioglass.

Lead zirconate titanate (Pb[ZrxTi1−x]O3 0<x<1), also called PZT, is a ceramic perovskite material that shows a marked piezoelectric effect.

Biocompatible polymers suitable in this invention may be methyl polymethacrylate (PMMA), polyethylene (PE), Poly-EtherEtherKetone (PEEK), polyglycolic acid (PGA), polybutylic acid (PBA), polylactic acid (PLLA), polycaprolactone (PCL)

According to a first embodiment, the biomaterial of the invention is non-resorbable and uses non-resorbable materials only. According to a second embodiment, the biomaterial is fully or partly resorbable.

According to a preferred embodiment, the three-dimensional biomedical device of the invention, having an osteoconductive first area with a controlled porosity and a second area, is such that the ratio of the porosity of the second area to the porosity of the first area being equal or less than one, preferably ranging from 0.001 to 0.9, preferably from 0.1 to 0.85, more preferably from 0.0111 to 0.83, more preferably ranging from 0.03 to 0.2, even more preferably from 0.033 and 0.166.

According to a particular embodiment, the three-dimensional biomedical device of the invention has an osteoconductive first area with a controlled porosity and a second area, is produced by a laser technology from a powder comprising a substantially not degradable hydroxyapatite, said powder being free of any metal or bone component, the ratio of the porosity of the second area to the porosity of the first area being equal or less than one, preferably ranging from 0.001 to 0.9 preferably from 0.1 to 0.85, more preferably from 0.0111 to 0.83, more preferably ranging from 0.03 to 0.2, even more preferably from 0.033 and 0.166.

Advantageously, the first area which is an osteoconductive porous matrix having a controlled porosity. The porosity (macroporosity) of the first area is preferably controlled by the 3D image laser. According to an embodiment, when the implant is placed in the defect, the first area, which is more porous than the second area, is contacting or close to the natural tissue bordering the defect. Advantageoulsy, the first area is at the periphery of the implant. Even more advantageously, the first area borders and surrounds the second area.

According to an embodiment, the pores of the first area have a diameter 10 to 1000 micrometers, preferably from 100 to 800 micrometers, more preferably from 200 to 600 micrometers, even more preferably 300 to 500 micrometers.

Advantageously the porosity of the matrix is controlled in such a way that the first area behave as an osteoconductive support. Advantageously, the porosity in the first area may range from 20 to 90 vol %, and preferably from 30 to 80 vol %. The term "vol %" means volume percentage, corresponding to the ratio of the volume of vacuity to the full volume.

According to another embodiment, the second area is such that its porosity is comprised between 0 and 25 vol %, preferably 0 and 10% vol % more preferably of about 0 and 5 vol %. Consequently, the properties of the implant in the second area are different from the properties of the implant in the first area. According to an embodiment, the second area occupies a larger surface in the implant that the first area.

According to an embodiment of the invention, the first area has a compression resistance ranging from 20 to 60 MPa, preferably ranging from 30 to 50 MPa, more preferably of about 40 MPa, the second area has a compression resistance of 80 to 150 MPa, preferably 90 to 120 MPa, more preferably of about 100 MPa.

According to an embodiment, the biomaterial of the invention is such that the first area and the second area are made from the same initial powder material, which preferably consists of synthetic hydroxyapatite only.

In this embodiment, the biomaterial of the invention is a three-dimensional multilayered biomedical device, having at least 2-1000 layers, preferably 5-500 layers, more preferably 10-400 layers, each layer being made from one powder material.

According to an embodiment, the biomaterial may be a composite biomaterial: in an embodiment, the biomedical has 2-1000 layers, least 2-1000 layers, preferably 5-500 layers, more preferably 10-400 layers, and at least two layers being made from non-identical powder materials.

Advantageously, the first and last layers are of one material, such as for example hydroxyapatite, and the inside layers are of a second material, such as for example a metal or metal alloy, advantageously titane or nitinol. In this embodiment, the finished implant may be such that its periphery is made of the one material, in our example hydroxyapatite, whereas its core is made of the second material, in our example metal or metal alloy.

In another embodiment, the material is made of a porous colonizable first area, which may be hydroxyapatite or tricalcium phosphate and a tight second area which may have a further function of reservoir for drug release.

In a further embodiment, the biomaterial of the invention includes a first peripheric area which may be hydroapatite, and a second core area, which may be TZP.

In a still further embodiment, the biomaterial of the invention includes a first area of hydroxyapatite, and a second area of ceramics such as for example zirconia, or metal or metal alloy.

In a still further embodiment, the biomaterial of the invention includes a first area of tricalcium phosphate, and a second area of ceramics such as for example zirconia, or metal or metal alloy.

The biomaterial of the invention may thus be non-uniformly porous. Non-uniform porosity allows for permeability (i.e. osteoconductivity) at some regions and not at others, within the biomaterial, or the extent of permeability may differ within the first area, if needed. According to an embodiment, the first area is gradated from a high porosity at its edge, to a lower porosity at its core.

According to another embodiment, the first and/or the second area includes spacers to make a biomaterial close to the alveolar bone, where the spacers play the role of the voids of the bone. The spacers are made of ceramics and are means for maintaining spaces, preferably a hollow space, within the biomaterial.

According to an embodiment, the biomaterial of the invention may comprise one or more pharmaceutical agents or biomolecules, or combinations thereof. The pharmaceutical agent may be any agent, although it is envisaged that the most useful agents will be those that e.g. promote healing, prevent infection, reduce inflammation, minimize or prevent pain, stimulate the influx of healing cells, or act as a immunosuppressant. The term "biomolecules" in this context includes cells, for example stem cells or progenitor cells. The biomolecules may be selected from the group consisting of: cells, cytokines, growth factors, hormones or combinations thereof.

In a particular embodiment of the invention, the first area, prior to implantation, is seeded or colonized by tissue forming cells immunologically compatible with the eventual implant recipient.

In a particular embodiment of the invention, the first area, prior to implantation, is seeded or colonized by tissue forming cells, such as for example stem cells or stem cells derived cells, which are preferably immunologically compatible with the eventual patient, more preferably autologous cells.

In a further embodiment, the first area, prior to implantation, is impregnated with a cell growth medium suitable for osteoblasts growth and/or is in contact or impregnated with growth factors. It may then seeded or colonized by tissue forming cells.

In a still further embodiment, the biomedical device of the invention is implantable.

In a preferred embodiment, the biomedical device of the invention is an implant, preferably a three-dimensional implant, more preferably a cranial implant. Preferably, this implant has a size suitable for large defects, preferably equal or larger than 25 cm$^2$, more preferably 28-100 cm$^2$. This implant may further comprise a sensor, such as for example a sensor of biological signals, preferably intracranial pressure detectors, electric micropotentials, etc.

In another embodiment, the biomedical device of the invention fits in a bone defect.

In another embodiment, the biomedical device of the invention is a coating, which is coated onto an implant.

This invention also relates to a method for manufacturing a biomedical device of the invention, wherein:

an image of the defect is performed through usual medical imagery means, such as for example MRI (magnetic resonance imaging), CT-scan (computerize tomography) and the image data are consolidated in a three-dimensionnal software such as for example "Mimics" of the MATERIALISE company in order to give a three-dimensionnal view;

from this image, a virtual object is designed with a computer-aid designed software known by one skilled in the art such as for example "3-Matic" of the Materialise company or "Cathia" of the Dassault Systems company;

optionally, a scale model (by model is meant a material subject matter), i.e. a larger or smaller object than the actual size of the virtual object designed with computer-aid software, or at the actual size of said virtual object, may be performed;

the design of the virtual object may be reviewed and optionally corrected by the surgeon or following the instructions of the surgeon;

upon agreement of the surgeon, the biomedical device is manufactured by a laser technology comprising layering a powder of particles, such as for example ceramic particles, more preferably substantially not degradable synthetic hydroxyapatite, onto a plate so that a layer of a predetermined thickness is formed on the plate, and having the laser beam selectively processed the powder to produce a processed layer, and this, layer after layer, the layers being joined together until the completed part is formed.

The method of the invention is advantageous, in that it makes it possible to directly manufacture biomedical devices, especially ceramic-based biomedical devices, without needing a molding step or a machining step.

The method of the invention is flexible, in that the design may perfectly be adapted to the defect and/or to the wishes of the surgeon.

According to an embodiment, the laser technology used in the process of the invention is laser powder fusion. In this embodiment, the particles of the powder are directly fused when contacted with the laser beam, thus the process of the invention avoids the use of any binding agent.

The process is performed from at least one powder of particles comprising ceramics; and/or metals; and/or metal alloys; and/or bioactive glasses; and/or lead zirconate titanate; and/or biocompatible polymers and/or mixtures thereof.

According to an embodiment, the particles consist of synthetic hydroxyapatite. Advantageously, for large defects this synthetic hydroxyapatite is substantially non-degradable. Preferably the hydroxyapatite powder has a purity of at least 95%.

According to another embodiment, the particles consist of tricalcium phosphate, preferably β-tricalcium phosphate.

According to a further embodiment, biphasic powder the particles comprise or consist of a mixture hydroxyapatite/tricalcium phosphate in a ratio ranging from 55/45 to 90/10.

In a specific embodiment, the powder may be a mixture of particles of various natures selected in the group of alumina, hydroxyapatite, B-TCP, Zircone and titanium, titanium alloys such as for example titanium-aluminium-vanadium, chrome-cobalt and alloys thereof.

The particles may have a granulometry of 1 to 500 micrometers, preferably 5 to 100 micrometers, more preferably 10 à 25 micrometers.

The plate may be slightly rough. This embodiment makes it easier for the first layer of particles to hook up onto the plate.

According to an embodiment, the layering device is a titanium plate, possibly coated with a film of hydroxyapatite prior to the beginning of the building of the piece; the coating may be carried out by a powder projection process such as for example "D gun". This kind of coating of the plate may help having a good hook of the powder on the plate, and may help the layering of the first layer.

According to an embodiment of the process of the invention, the powder is layered with a layering device; the layering device may be a roll, such as for example a ceramic roll. According to another embodiment, the layering device is a blade, such as for example a metallic blade.

The thickness of the layer of powder may be adjusted at a predetermined value, which may for example be of 10 to 1000 micrometers, preferably of 50 to 500 micrometers, more preferably 70 to 100 micrometers.

According to an embodiment, the powder may be heated prior to the layering step, at a temperature of 200 to 1500° C., preferably of 500 to 1200° C., more preferably of about 800° C. The prior heating of the powder may facilitate the processing of the powder.

According to the invention, the laser locally impacts the powder. The laser may be a pulsed laser or a continuous laser, preferably of 100 to 250 watts, preferably of 160 watts. In an embodiment, the laser may be a laser YAG. The laser power of the laser beam may be adjusted at 1 to 25% of the total power of the laser, preferably at 5%, 7% or 10% of the total power. The laser may be partially defocused (for example 10% of defocusing).

At the point of impact of the laser, the powder of particles fuses. The trajectory of the laser, which is defined by computer means to reproduced the computer-aid designed object, defines the shape of the object made from the processed particles, in the thickness of the layer.

The progression speed of the laser beam may range from 0.01 and 50 mm/s, preferably from 0.1 and 10, more preferably from 1 and 4 mm/s.

When a layer is processed, a further layer is spread and laser processed. The trajectory of the laser may have a deviation between the laser beams and the deviation may range from 50 to 150 micrometers, preferably from 70 and 110 micrometers.

According to an embodiment, the plate is supported by a tray and the tray is movable up and down. In this embodiment, when a layer is processed, the tray is moved down prior to the processing of the next layer.

According to another embodiment, the plate is located within a container, which is preferably tight. Preferably, the container is a furnace or an oven, so that the powder may be easily heated.

Layer after layer, with reference to the 3D designed object, the full biomedical device is made. The non-processed powder is blown out.

According to an embodiment, a further optional step of thermic post-treatment may be performed, wherein the biomedical device is reheated at a temperature of 200 to 400° C., preferably 250 to 350° C., more preferably around 300° C. The final biomedical device is then recovered.

Another object of the invention is the use of a biomedical device according to the invention for replacing or filling of tissue defects, e.g. bone defects or cavities in animals, including humans.

According to an embodiment, the biomedical device of the invention may be used as an implant repairing defects in bone structures resulting from surgery or trauma. In this embodiment, the biomedical device of the invention may be useful to close a defect, such an opening in a skull, to protect the tissue underneath, e.g. brain tissue.

Thus, the biomedical device of the invention is an orthobiological device, resulting in a porous scaffold. It may be used in traumatology, in reconstruction surgery, in regenerative surgery, in dental surgery, in orthodontia, in orthopaedic, in cell culture or any field of application which could benefit from permanent biocompatible but substantially not degradable implant for reconstructive purposes or for functional purposes like drug delivery or pick-up of inner signals (intracranial pressure or electric potentials for instance) or transmission of signals and/or energy from outer side of the body to inner side and vice versa.

More specifically, the biomedical device of the invention may be used as an implant to compensate bone losses such as: cranial lesions, calveria lesions, due to traumas, tumors or malformation; maxillofacial bone losses (orbital and maxillary); dental lesions with significant loss of alveolar bone.

Also, the biomedical device of the invention may be used as an implant to compensate bones losses in orthopaedic indications such as for example traumatic lesions hard to consolidate, typically significant segmental bone losses such as tibial pseudarthroses or non-union; primary bone cancer, tipically Ewing sarcoma at the proximal femur; hip replacement.

According to another embodiment, the biomedical device of the invention may be a synthetic bone, preferably a hydroxyapatite synthetic bone, on and/or in which stem cells, preferably autologous stem cells, may have been seeded and/or cultured.

According to a particular embodiment, this invention is directed to an orthopedic implant for implantation into bone cavities to support bone tissue adjacent to the cavity.

The present invention will become more fully understood from the detailed description given herein below and the accompanying drawings which are given by way of illustration only, and are not intended to limit the scope of the present patent application.

FIG. 1 is schema of a suitable device to implement the process of the invention.

EXAMPLE

The machine used may be a Phenix® PM100 device commercialized by Phenix Systems®.

A ceramic powder of hydroxyapatite having a granulometry 10 to 25 micrometers (commercial reference Medicoat®/Medipure® 20-15, purity>95%) is placed in a container 1 so that it can be layered on a plate 2. The tray 2 may be located in the furnace 3 of the machine 6. The powder may be heated to 800° C. The plate 2 may be supported by a tray 10 movable up and down. The powder is layered with a ceramic roll 5 at a place 7, where it will be processed by a laser beam 8 release from a galvanometric head 9 (computer directed optical susceptible to direct a laser beam with high speed and high precision). The thickness of the resulting layer is of about 100 micrometers. A laser YAG 160 Watts is preferably used to locally impact and process the powder. The power of the laser beam may preferably be adjusted to 10% of the total power of the laser in order to avoid vitrification of the ceramic powder; the laser beam may be 10% defocused; the laser deviation may be 80 micrometers; the progression speed of the laser beam may be of 4 mm/s. The trajectory of the laser is defined by the 3D-image.

The data of the image (CT scan or IRM for example) are exported in a suitable format, for example DICOM. This file is imported in a software which carries out a partition of the various level of grey and, starting from various cut-offs, rebuilds the three-dimensional anatomy of the defect. From this 3D file and a computer mediated design software, it is possible to conceive the macrostructure of the implant that fits the defect.

A first area, preferably located at the periphery of the structure, may be a matrix-type microstructure colonizable by the patient's osteoblasts.

The design of the implant is exported in a suitable format (for example format STL,IGES,DXF,HPP,OBJ) to the rapid prototyping machine, and is cut-off in slices corresponding to the thickness of the layers (for example, format SLC). The information for each layer defines the trajectory of the laser.

The trajectory of the laser designs the shape of the 3D-image in the powder, actually in the thickness of the powder. When a layer is processed, the tray supporting the plate is moved down at a distance corresponding to the thickness of a layer and the next layer of powder is layered. The process is repeated until the full biomedical device is produced. The laser beams processes, preferably fuses the ceramic particles together in the whole thickness of the layer and it action propagates also on the preceding layer, so that the current layer and the preceding layer actually are fused together.

At the end of the process, the not-fused residual powder is blown out by any suitable means, preferably mechanical means such as for example micro-aspiration or suction or brushing; then, the biomedical device is recovered.

The invention claimed is:

1. A method for manufacturing a biomedical device for fitting bone defect, said biomedical device having an osteoconductive first area, at the periphery of the biomedical device, with a controlled porosity and a second area with a porosity, the ratio of the porosity of the second area to the porosity of first area being equal or less than one, and the device being produced by a laser technology from a powder comprising a material selected from the group consisting of ceramics, metals, metal alloys, bioactive glasses, lead zirconatetitanate, biocompatible polymers, and mixtures thereof, wherein the laser is a pulsed laser or continuous laser of 100 to 250 watts the laser power of the laser beam being adjusted at 1 to 25% of the total power of the laser and the progression speed of the laser beam ranging from 0.01 and 50 mm/s, and wherein
   an image of the defect is performed,
   from this image, a virtual object is designed with a computer-aid designed software,
   optionally, a scale model is performed,
   the biomedical device is manufactured by a laser technology comprising layering a powder of particles onto a plate (7) so that a layer of a predetermined thickness is formed on the plate (7), and having the laser beam (8) selectively processed the powder to produce a processed layer, and this, layer after layer, the layers being joined together until the completed biomedical device is formed.

2. The method according to claim 1, wherein the particles have a granulometry of 1 to 500 micrometers.

3. The method according to claim 1, wherein the thickness of the layer of powder ranges from 10 to 1000 micrometers.

4. The method according to claim 1, further comprising a step of heating the powder prior to the layering step, at a temperature of 200 to 1500° C.

5. The method according to claim 1, wherein the laser is a 160 watts laser.

6. A method for replacing or filling of tissue defects, preferably bone defects in animals, including humans, comprising manufacturing a biomedical device fitting said tissue defect, said biomedical device having an osteoconductive first, at the periphery of the biomedical device, with a controlled porosity and a second area with a porosity, the ratio of the porosity of the second area to the porosity of first area being equal or less than one, and the device being produced by a laser technology from a powder comprising a material selected from the group consisting of ceramics, metals, metal alloys, bioactive glasses, lead zirconatetitanate, biocompatible polymers, and mixtures thereof, wherein the laser is a pulsed laser or continuous laser of 100 to 250 watts the laser power of the laser beam being adjusted at 1 to 25% of the total power of the laser and the progression speed of the laser beam ranging from 0.01 and 50 mm/s, and wherein
   an image of the defect is performed,
   from this image, a virtual object is designed with a computer-aid designed software,
   optionally, a scale model is performed,
   the biomedical device is manufactured by a laser technology comprising layering a powder of particles onto a plate (7) so that a layer of a predetermined thickness is formed on the plate (7), and having the laser beam (8) selectively processed the powder to produce a processed layer, and this, layer after layer, the layers being joined together until the completed biomedical device is formed.

7. The method according to claim 6, wherein the thickness of the layer of powder ranges from 10 to 1000 micrometers.

8. The method according to claim 6, further comprising a step of heating the powder prior to the layering step, at a temperature of 200 to 1500° C.

* * * * *